United States Patent [19]
Tucker et al.

[11] Patent Number: 5,807,343
[45] Date of Patent: Sep. 15, 1998

[54] PROTECTIVE SEALING BARRIER FOR A SYRINGE

[75] Inventors: Robyn Laurie Tucker, Ridgewood; Sandor Gyure, West Orange; Robert B. Odell, Franklin Lakes, all of N.J.

[73] Assignee: Becton Dickinson and Company, Franklin Lakes, N.J.

[21] Appl. No.: 723,489

[22] Filed: Sep. 30, 1996

[51] Int. Cl.⁶ ................................................. A61M 5/00
[52] U.S. Cl. .......................... 604/187; 604/111; 604/192
[58] Field of Search ...................................... 604/187, 192, 604/110, 111, 263

[56] References Cited

U.S. PATENT DOCUMENTS 3,989,044 11/1976 Meierhoefer ............................ 604/192
3,989,045 11/1976 Van Eck ............................... 604/192 X
4,148,316 4/1979 Xanthopoulos .......................... 604/192

*Primary Examiner*—John D. Yasko
*Attorney, Agent, or Firm*—Allen W. Wark

[57] ABSTRACT

A protective sealing barrier for a syringe is disclosed. The protective sealing barrier can be configured to safeguard the sterility of the syringe and any contents held therein, as a barrier against leakage of any contents held within the syringe, or both. The syringe includes a luer tip and a collar having terminal ends which are preferably substantially co-planar with one another. The barrier consists of a membrane which is disposed in substantially entire surface contact with the terminal ends of both the luer tip and the collar. The membrane can be selected from a material permitting the syringe to be irradiated or heat sterilized. Likewise, the membrane can be chosen from a material permitting the syringe to be sterilized by various gas sterilization procedures. The membrane provides good tamper evidence of the syringe, can be stocked in a uniform size adaptable to various sizes of syringes, reduces the storage space required for the syringes, and can serve as a platform for printing information regarding contents held within the syringe.

14 Claims, 6 Drawing Sheets

PROTECTIVE SEALING BARRIER FOR A SYRINGE

FIELD OF THE INVENTION

The invention relates to a protective sealing barrier for a syringe, and more particularly, to a protective sealing barrier for a syringe which can be configured for sterility maintenance or leak avoidance, or both, and which can be detached by an end-user prior to use of the syringe.

BACKGROUND

As is known in the art, syringes are medical delivery devices utilizable to administer a medicament to a patient. Syringes can be shipped empty in a sterile state and filled by an end-user, for instance, from a vial or other source of medicament at the time administration of the medicament is desired. Alternately, syringes can be of the prefillable form, wherein a set dosage of medicament can be pre-filled into the syringe by a pharmaceutical manufacturer for distribution to the end user.

In either case, syringes typically include a barrel portion adapted to retain the medicament. The barrels are normally configured of plastic or glass materials. The distal end of the barrel is normally configured to mate with a conventional piercing element, such as a pointed needle cannula made of steel or like material or a blunt ended cannula formed of plastic, to deliver the medicament contained in the barrel. In some syringes, the piercing element is attached to the syringe as an integral part of the distal end of the syringe barrel. An example of such a syringe is the HYPAK® brand prefillable syringe manufactured by Becton Dickinson Pharmaceutical Systems of Le Pont de Claix, France.

In other syringes, the piercing element is attached to the syringe when use of the syringe is desired. There are a number of basic kinds of such syringes. An example of such a syringe is the luer tip syringe. In a luer tip syringe, the hub of a piercing element is connected to a luer tip associated with the syringe. Another type of such syringe is the luer lock syringe. In a luer lock syringe, the luer tip is surrounded by a threaded collar. The hub of the piercing element is inserted over the luer tip and threadedly engaged to the collar.

In any of the aforementioned syringes, a plunger rod is inserted through the open distal end of the syringe barrel and, through its engagement with an elastomeric or rubber-like stopper element fitted in a fluid-tight manner within the interior of the barrel, a user can apply manual force to the plunger to deliver the medicament through the piercing element.

Whether the syringe is of the type that will be filled by the end user, or whether the syringe is of the prefillable type that is to be filled by a pharmaceutical manufacturer, there is a need to maintain the sterility of the syringe until such time as it is used to deliver a medicament. Where the syringe is of the prefillable type, it is also important to maintain the sterility of any drug stored within the barrel until such time as use of the drug is desired. It is further necessary in prefillable syringes to provide a fluid seal such that the medicament does not leak from the syringe barrel. For instance, where the syringe has a fixed needle, such as the HYPAK® brand prefillable syringe, a rubber needle guard is inserted over the piercing element. The needle guard seals the fluid path to the drug held in the syringe barrel while at the same time protects the medicament against contamination.

Another prior art approach for providing a fluid seal and for maintaining the sterility of a syringe is illustrated in FIG. 1. Here, a luer lock syringe 10 is depicted, and it includes a barrel 16 characterized by a proximal end 14 and a distal end 12. A luer collar 18 is formed adjacent the distal end of the syringe barrel. Luer collar 18 is characterized by a plurality of internal threads 20. As is true of luer lock syringes, a luer tip 22 conventionally extends beyond the distal end of luer collar 18, and is disposed for fluid communication with interior portions of the syringe barrel. Each of the syringes is typically provided with a plastic luer lock tip cap 24 to seal luer tip 22. Internal portions of luer lock tip cap 24 are configured to receive luer tip 22 and to mate with the exterior surface of luer tip 22. Luer lock tip cap 24 includes one or more threads 26 configured to mate with internal threads 20 associated with the luer collar.

While generally sufficing to provide a fluid seal and to maintain the sterility of various components of the syringe, including the luer tip and the interior of the syringe barrel, certain improvements can be realized to the aforementioned approach. Generally, external means of tamper evidence are necessary, in that the luer lock tip cap is threadedly engaged with the luer collar, and relying on the threaded structure alone, it is difficult to detect if the tip cap has been threadedly disengaged from the luer collar. Also, owing to frictional forces between the plastic parts, and depending on how tightly the luer lock tip cap is applied to the collar, it can be difficult to remove the luer lock tip cap from the luer collar. Moreover, while the luer lock tip cap is a relatively small unit, it would be beneficial to further minimize the quantity of waste which has to be disposed of after the syringe is used.

SUMMARY OF THE INVENTION

These and other concerns are addressed by a protective sealing barrier for a syringe in accordance with the present invention. Depending on the functions required, the protective sealing barrier can be configured for sterility maintenance, for leakage maintenance, or both. The syringe, which can be made of plastic or glass, includes a luer tip and a collar surrounding the luer tip. In a preferred embodiment, the terminal ends of the luer tip and collar are substantially co-planar. The collar can be threaded, if desired.

In a preferred embodiment, the protective sealing barrier is configured as a relatively flat membrane disposed over the terminal ends of both the luer tip and the collar in substantially complete surface contact with the terminal ends. The membrane can be peelable from the terminal ends of the luer tip and collar when it is desired to attach a conventional needle hub in order to deliver medicament from the syringe.

The material selected for the membrane can be chosen in order to provide sterility maintenance or to safeguard against leakage, or both. For instance, the membrane can be formed from a single material, or from a combination of materials arranged in desired configurations, to provide either sterility maintenance or leakage maintenance, or both. The material selected for the membrane can be chosen such that it is suitable for various irradiation or heat sterilization procedures. For instance, the membrane can be formed from a single material, or from a combination of materials arranged in desired configurations, which exhibit good heat resistance and which are able to withstand heat and pressure changes generated during the sterilization procedure. Similarly, where it is desirable to employ gas sterilization techniques, the single material, or the combination of materials arranged in desired configurations, can be chosen to exhibit hydrophobic properties while at the same time being gas porous.

The membrane can be sourced from a stock size to fit any of the various sizes of syringes manufactured. The membrane provides a leak-proof or sterility maintenance seal, or both, for the internal fluid path of the syringe as well as for the outside portions of the luer tip and internal portions of the luer collar, both of which will be urged into contact with the needle hub of a piercing element. The membrane is easily disposed of and provides accurate tamper evidence for the syringe in a manner which is easily operated by an end user.

In an alternate embodiment, the syringe may be configured as a luer lock syringe, wherein the distal end of the luer tip extends past the distal end of the luer collar. Rather than assuming a flat configuration, the membrane can be shaped or otherwise configured to accommodate the protruding portion of the luer tip. The membrane is configured to make substantially complete surface contact with the terminal ends of the luer tip and the luer collar.

BRIEF DESCRIPTION OF THE DRAWINGS

The invention will now be described in greater detail by way of reference to the appended drawings, wherein.

DETAILED DESCRIPTION OF THE INVENTION

Figure 1:
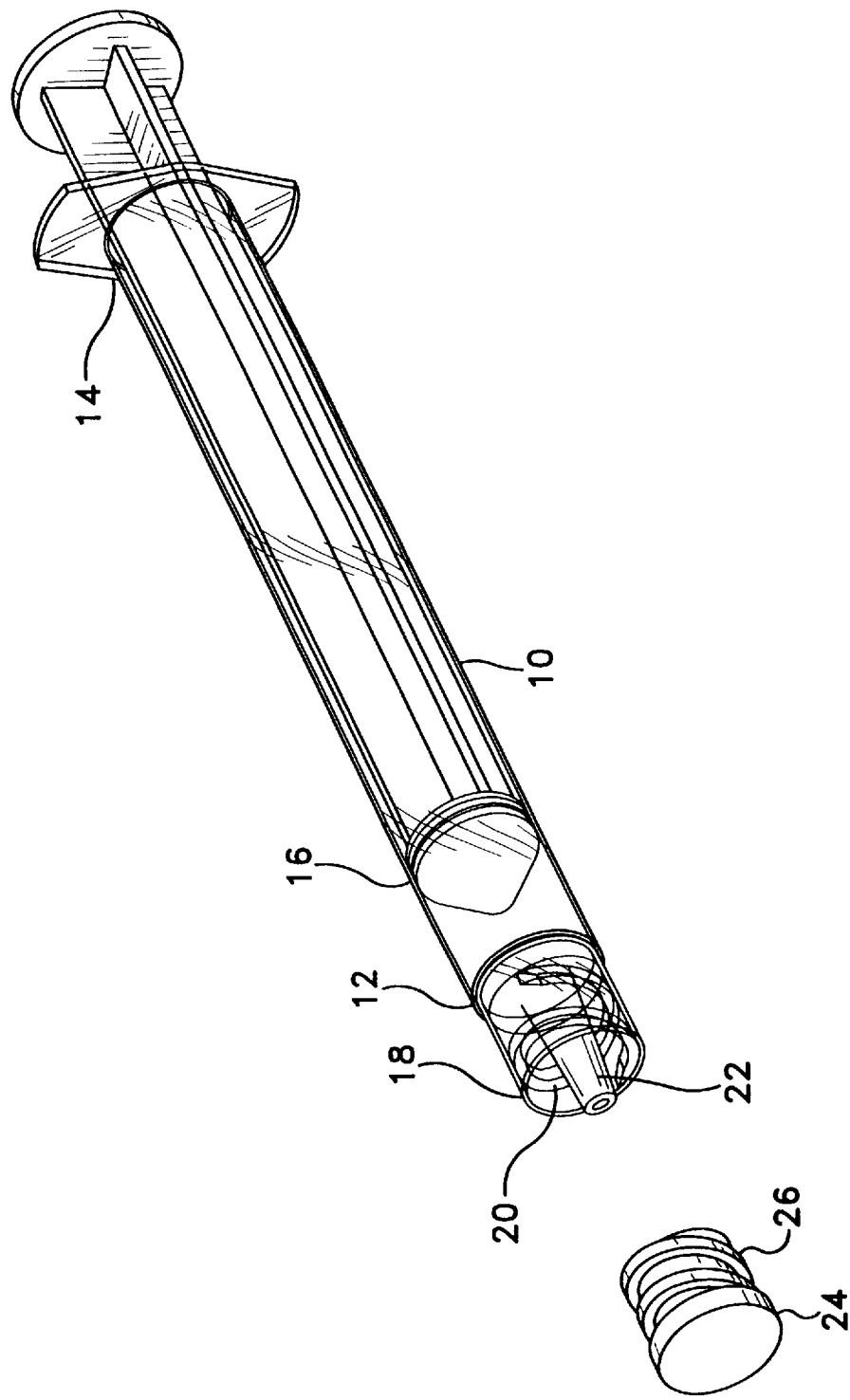
FIG. 1 depicts, in perspective view, a prior art manner for effecting a fluid seal and a sterility barrier in a luer lock syringe.
Figure 2:
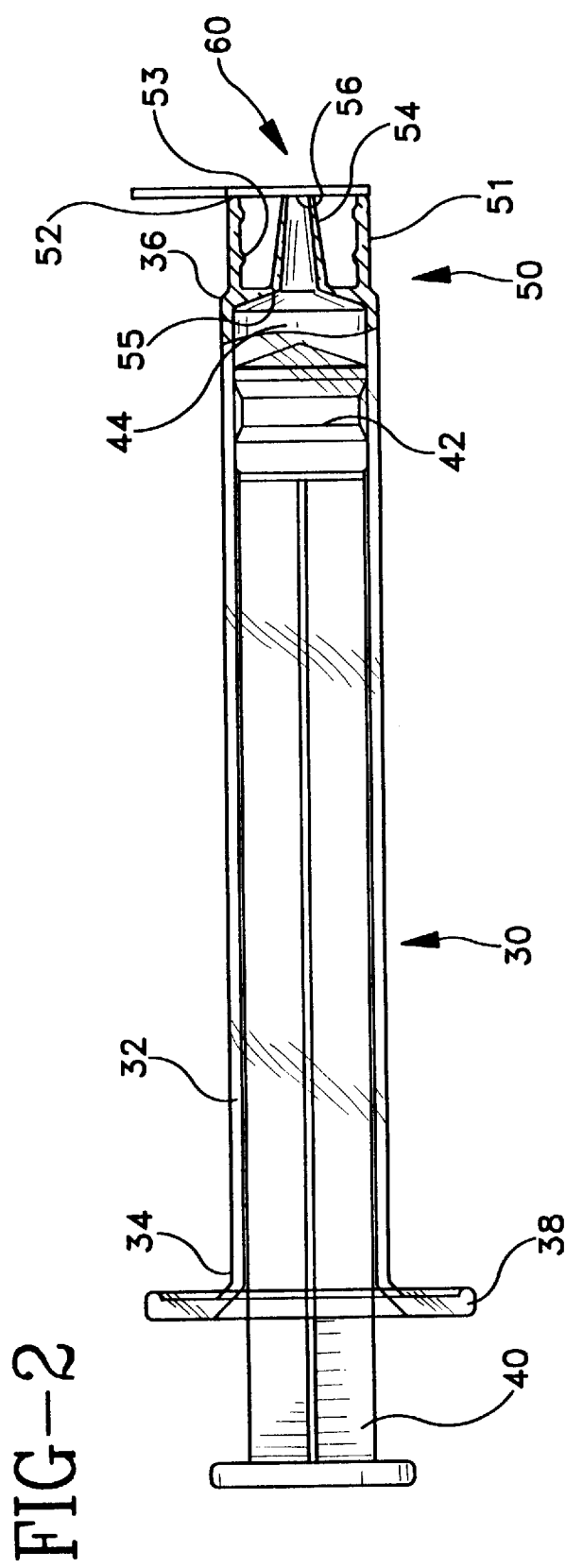
FIG. 2 depicts, in cross-sectional view, one embodiment of a protective sealing barrier for a syringe in accordance with the present invention.
Figure 3:
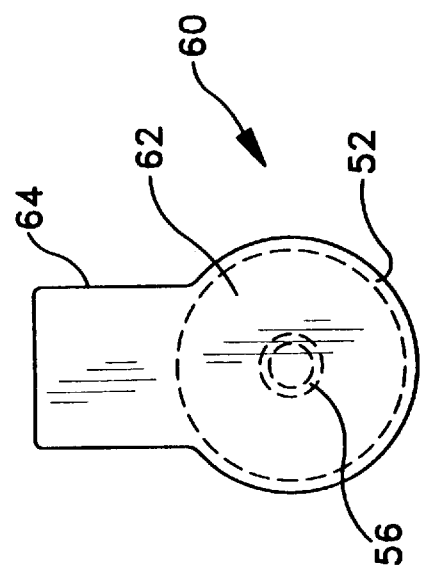
FIG. 3 depicts a top view of the protective sealing barrier illustrated in FIG. 2.

A convention utilized throughout this description is that the term "distal" refers to the direction furthest from a practitioner, while the term "proximal" refers to the direction closest to a practitioner.

It will be understood by the skilled artisan that the protective sealing barrier in accordance with the present invention can be employed with syringes intended to be filled by an end user, for instance, from a source of medicament such as a vial. The protective sealing barrier can also be employed for syringes of the prefillable type, which are normally filled with a quantity of medicament by a pharmaceutical manufacturer before being shipped to an end-user. Depending on the functions required, the protective sealing barrier may be configured for sterility maintenance, to provide a barrier against leakage, or both. For instance, where the syringe is empty until use is desired, then the barrier need only be configured for sterility maintenance. However, where the syringe is of the prefillable type and is to be filled with a quantity of medicament prior to shipment to an end-user, then the barrier is preferably configured as a leak-proof barrier, and if external means for sterility maintenance are not provided, to also act as a sterility barrier.

Also, solely for ease of reading and explaining the principles of the present invention, the terms "luer tip" or "luer lock" tip are frequently recited in this application. As the skilled artisan will appreciate, the terms "luer tip" or "luer lock" tip each designate a frusto-conically shaped fluid tip which is shaped or otherwise dimensioned to an appropriate standard such as standards specified by the International Standards Organization ("ISO"). It will be understood by the skilled artisan, however, that the benefits and advantages provided by the protective sealing barrier according to the present invention are not limited strictly to fluid tips configured to the ISO "luer tip" or "luer lock" tip standards. Rather, the protective sealing barrier in accordance with the present invention is broadly applicable to any fluid tip configured to a non-ISO standard dimension. It will be understood by the skilled artisan, then, that the patent claims appended hereto are intended to encompass fluid tips dimensioned or otherwise shaped outside of the ISO standards for "luer tips" or "luer-lock" tips.

Turning now to the drawings, wherein like numerals denote like components, FIGS. 24 depict one embodiment of a syringe 30 which can enjoy the benefits of the protective sealing barrier of the present invention. Syringe 30 includes a barrel 32 having a proximal end 34 and a distal end 36. A flange 38 may be provided about the proximal end to enhance a user's digital manipulation of the syringe. Plunger rod 40 is inserted to a proximal end 34, and it mates with a stopper element 42 held within barrel 32. Syringe 30 can be of the type intended to be filled by the end-user prior to use, or it can be of the pre-fillable type, which is supplied to a pharmaceutical manufacturer to enable the pharmaceutical manufacturer to process the syringe such that it holds a charge of medicament 44 within the syringe barrel prior to distribution to the end user.

As has been pointed out, a general concern in syringes is the ability to maintain the sterility of the syringe, and particularly the various fluid paths contained within the syringe, until such time as use is desired. Where the syringe is prefilled with a charge of medicament 44, it is also necessary to safeguard the sterility of the medicament until such time as the syringe is intended for use. Also, where the syringe is prefilled with a medicament 44, another concern is to ensure that medicament 44 not leak out of barrel 32. Accordingly, syringe 30 in accordance with the present invention includes a protective sealing barrier which can be configured for sterility maintenance or for leakage maintenance, or both, to address the difficulties encountered in the aforementioned prior art approaches.

In general, syringe 30 includes fluid path structure 50 for mating the hub of piercing element, such as the hub of a needle cannula (not shown) to the syringe to deliver a charge of medicament 44 either prefilled by a pharmaceutical manufacturer into, or filled by the end-user into, the syringe barrel. Fluid path structure 50 includes a collar 51 provided about distal end 36 of the syringe. If desired, interior portions of collar 51 may include one or more threads 53 configured to mate with complimentary threads (not shown) associated with the hub of a piercing element employed to deliver medicament 44 from barrel 32. Collar 51 includes a terminal end 52.

A luer tip 54 is provided within the interior of collar 51. Luer tip 54 includes a proximal end 55 disposed in fluid communication with barrel 32. In a preferred embodiment, luer tip 54 also includes a terminal end 56 which is substantially co-planar with terminal end 52 associated with collar 51. Unlike conventional luer lock syringes known in the art, wherein the luer tip extends from the luer collar (see FIG. 1), here, luer tip 54 and collar 51 include terminal ends which are preferably substantially co-planar, i.e., the luer tip does not extend beyond the distal end of the collar.

Syringe 30 includes a protective sealing barrier covering fluid path structure 50. Here, the protective sealing barrier may be configured as a membrane 60 disposed in substantially entire surface contact with the terminal ends 52, 56 of the collar and luer tip, respectively. In a preferred embodiment, membrane 60 is configured with a relatively flat structure, including a planar portion 62 configured to entirely cover terminal end 52 of collar 51 and terminal end 56 of luer tip 54.

Membrane 60 is designed so as to be removable from syringe 30 when use of the syringe is desired. In this vein, membrane 60 can be affixed to the terminal ends of the collar and luer tip in various ways. For example, membrane 60 can be separately supplied from collar 51 and luer tip 54 and affixed to them via adhesives, welding, heat-sealing or the like. Practically speaking, membrane 60 may also be formed with the luer tip, for instance, via a co-injection process, with a construction facilitating the removal of the membrane from the collar and luer tip. For example, molding tools can be implemented so as to form at least the portion of membrane 60 that is affixed over luer tip 54. The remainder of membrane 60 can be formed separately and affixed to collar 51 and luer tip 54.

To assist the user in removing membrane 60 from the syringe, a pull-tab 64 is provided adjacent planar portion 62. Simply, a user can remove membrane 60 from fluid structure 50 by pulling on pull-tab 64.

Figure 4:
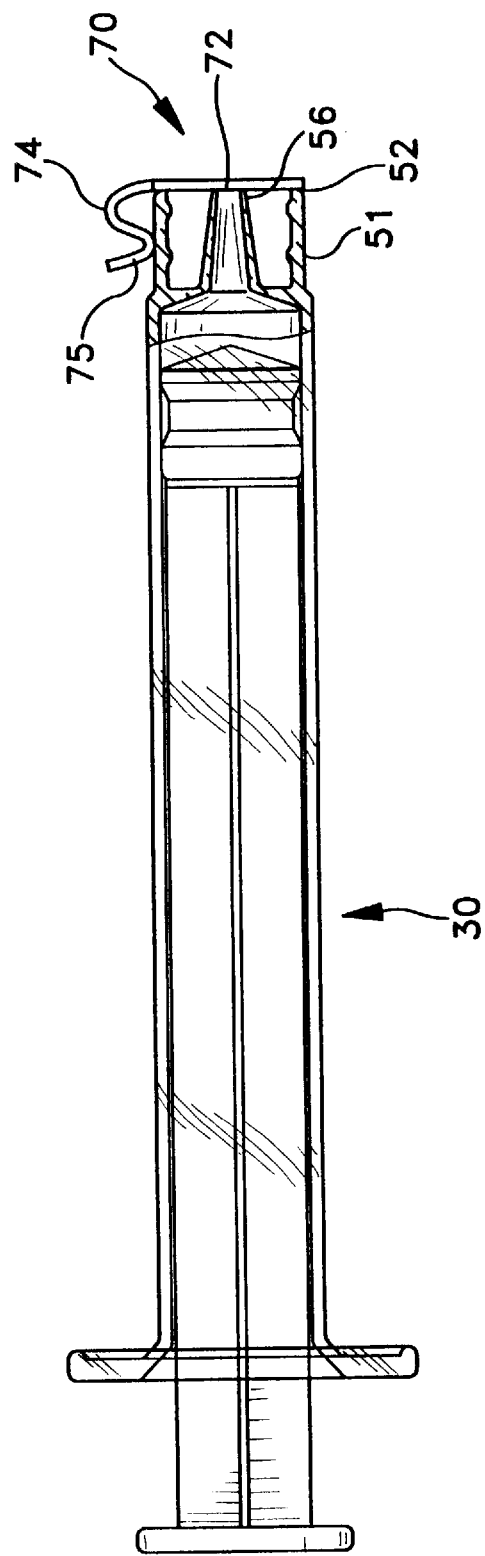
FIG. 4 is a cross-sectional view of an alternative embodiment of a protective sealing barrier for a syringe in accordance with the present invention.

FIG. 4 illustrates an alternate configuration of a protective sealing barrier in accordance with the present invention. Here, membrane 70 includes a planar portion 72 and a pull tab 74. Pull tab 74 is attached at a location 75 intermediate an end 74 of the pull tab to some area of prefillable syringe 30 so as to prevent inadvertent detachment of membrane 70 until desired. Here, pull tab 74 is attached to the exterior surface of collar 51, for instance, by adhesives, welding, co-injection, or the like.

If desired, terminal ends 52 and 56 can be roughened, contoured, shaped or otherwise configured in a manner to enhance the adhesion of membrane 60 (70) to the terminal ends. Terminal ends 52 and 56 may also be subjected to certain surface processing treatments, such as corona or plasma treatments, for the same purpose. The co-planar configuration of terminal ends 52 and 56 contributes to allowing the membrane to make substantially entire surface contact with them. This allows the membrane 60 (70) to act as a good fluid barrier while at the same time maintaining the sterility of fluid structure 50, including any medicament 44 that may be contained within the syringe barrel.

Figure 5:
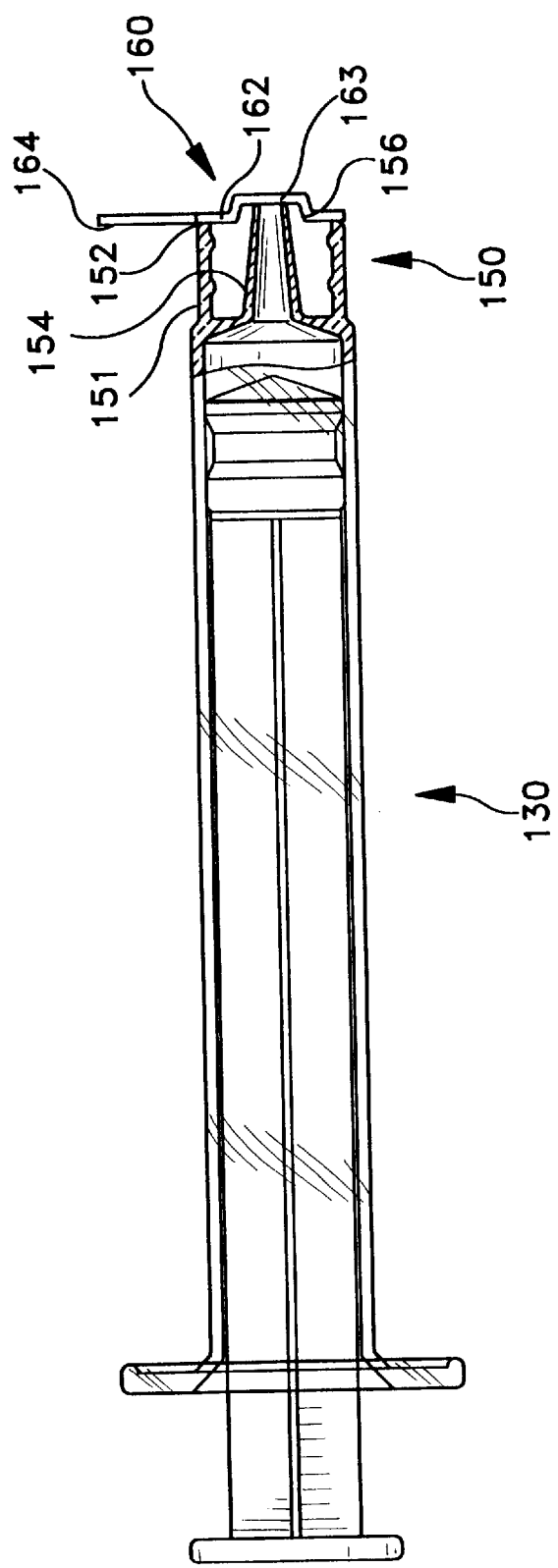
FIG. 5 depicts an alternate embodiment of a protective sealing barrier for a luer lock syringe.
Figure 6:
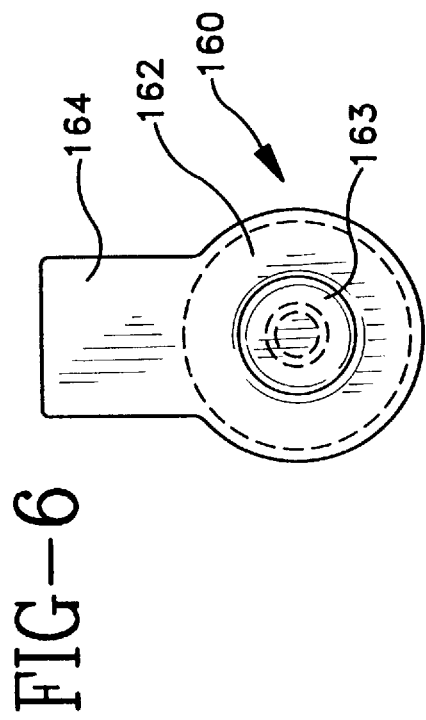
FIG. 6 is a top view of the protective sealing barrier of FIG. 5.

FIGS. 5 and 6 depict an alternate embodiment of a protective sealing barrier in accordance with the present invention, suitable for application to a luer lock syringe. As has been previously explained, in a luer lock syringe, a luer tip 154 conventionally extends past the distal end of a luer collar 151. Hence, terminal end 156 of luer tip 154 extends beyond terminal end 152 of luer collar 151. The protective sealing barrier in accordance with the present invention can feature a membrane 160 configured for sealing contact with the terminal ends of luer tip 154 and luer collar 151, so configured. Particularly, membrane 160 includes a planar portion 162 configured to entirely cover terminal end 152 of luer collar 151.

Figure 7:
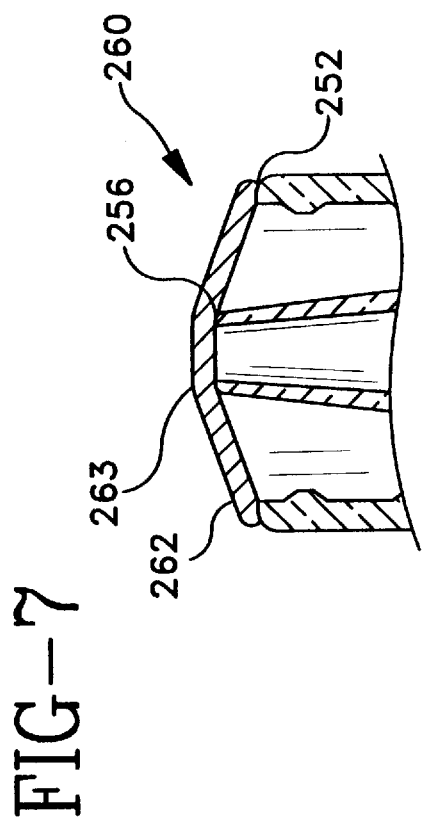
FIG. 7 depicts a further alternate embodiment of a protective sealing barrier in accordance with the present invention.

Membrane 160 also features a tent-like protrusion 163 to accommodate the protruding portion of luer tip 154. Tent-like protrusion 163 can be pre-formed into the structure of planar portion 162. Alternately, tent-like protrusion 163 can be created during the application of the membrane to the syringe. In either case, the tent-like protrusion is configured to make substantially complete surface contact with terminal end 156 of luer tip 154. As herein configured, tent-like protrusion 163 takes a cup-like shape, such that the tent-like protrusion does not contact external portions of luer tip 154, apart from terminal end 156. However, referring to FIG. 7, it will be appreciated by the skilled artisan that if so desired, tent-like protrusion 263 can be realized as the structure which is created by simply draping membrane 260 between terminal end 256 of the luer tip and terminal end 252 of the collar and affixing the membrane thereto. If also desired, the tent-like protrusion may also be configured to make surface contact with exterior portions of the luer tip. The characteristics of the membrane accordance with this embodiment, such as the ability to configure the membrane for various sterilization procedures, have been previously explained.

Figure 8:
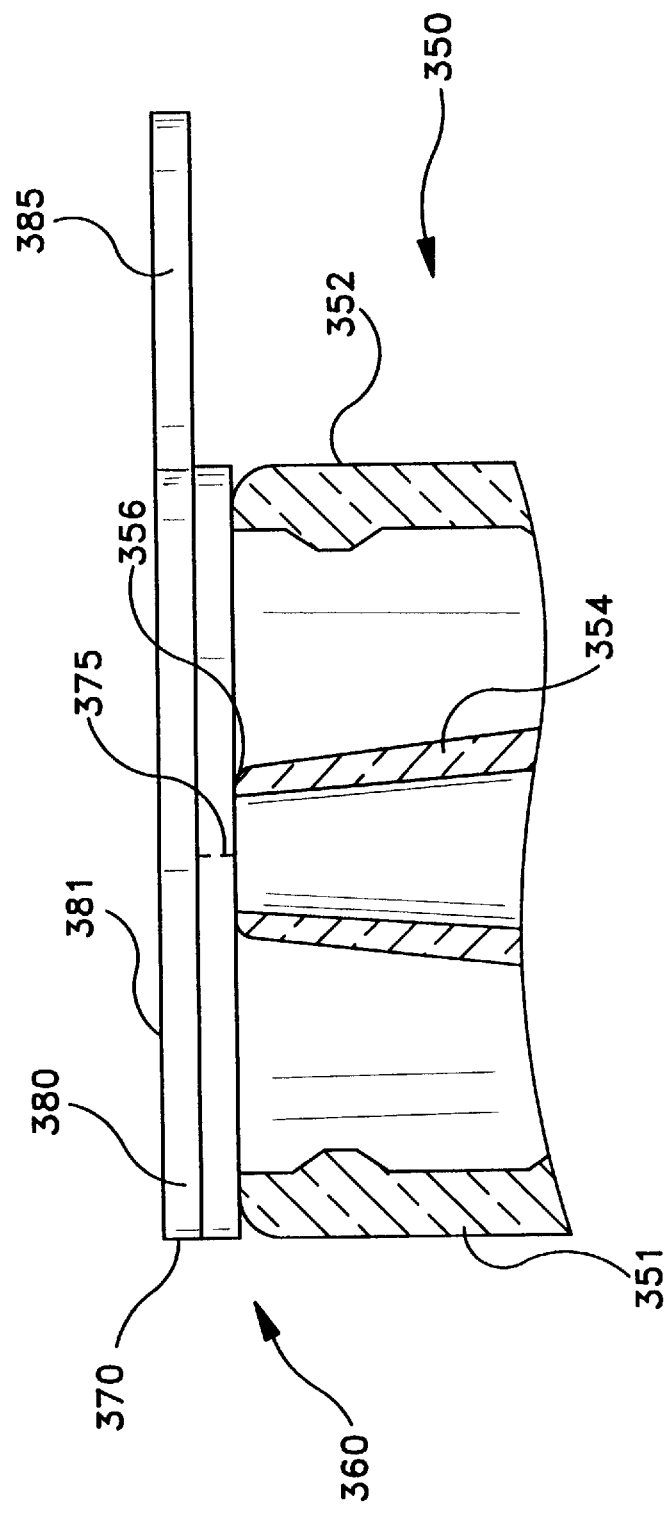
FIG. 8 depicts a further alternate embodiment of a protective sealing barrier in accordance with the present invention.

FIG. 8 depicts an embodiment 360 of a protective sealing barrier in accordance with the present invention, employing a multi-layer configuration. As before, the syringe includes a fluid structure 350 which features a luer tip 354 and a collar 351. Preferably, the terminal ends 356, 352 of the respective luer tip and collar are substantially co-planar. Protective sealing barrier 360 is comprised of a multi-layer configuration, including a bottom-layer 370 which, as depicted, is directly in entire surface contact with the terminal ends 356, 352 of the luer tip and collar, respectively, and an upper-layer 380 attached to bottom layer 370. A pull-tab 385 is provided to upper-layer 380. If desired, bottom layer 370 need only cover terminal end 356 of the luer tip, with upper layer 380 serving to cover terminal end 352 of the collar.

When it is desired to use the syringe, upper layer 380 is removable by an end-user to expose bottom layer 370. In a preferred form, bottom-layer 370 is employed for sterility maintenance, i.e., bottom layer 370 is configured as a sterility barrier about luer tip 354 and barrel 351. Upper layer 380 need not be sterility-maintaining, and in fact, outer surface 381 of the upper layer need not be sterile. A user need not remove the bottom-layer 370 from the syringe in order to use the syringe. Simply, a user may pierce bottom-layer 370 at terminal end 356 of the luer tip prior to connecting a piercing element to the syringe.

Alternately, the bottom layer 370 can feature a pressure-sensitive burst point 375 disposed directly over terminal end 356 of luer tip 354. Pressure-sensitive burst point 375 can entail, for instance, a weakened section of bottom-layer 370. When a user mates the hub of a piercing element (not shown) about luer tip 354 and exerts fluid pressure, either by aspirating medicament into the syringe or by expelling medicament held within the syringe (not shown), pressure-sensitive burst point 375 will open, permitting fluid to flow through terminal end 356 of luer tip 354.

It will be appreciated that by the construction of FIG. 8, bottom layer 370 can provide a sterility-barrier, while upper layer 380 can be configured as a leak-proof barrier.

It will be appreciated by the skilled artisan that in lieu of effecting removal of the membrane from the syringe in order to gain access the luer tip, the foregoing protective sealing barriers described in FIGS. 2–7 can be pierced in the area of the luer tip, as described for FIG. 8 herein. Alternately, the foregoing protective sealing barriers described in FIGS. 2–7 may incorporate the pressure-sensitive burst-point features described for FIG. 8 herein so as to gain access to the luer tip.

It will be realized by the skilled artisan that the configuration of the protective sealing barrier presented herein provides many benefits over conventional products in the prior art, such as luer lock tip cap 24. For example, the membrane can be formed from materials suitable to facilitate the processing of syringe 30 in accordance with the material selected for the syringe, a pharmaceutical company's processing of syringe 30 (particularly giving consideration to medicament 44 intended to be held therein), or the like. They can also be selected in accordance with the function—sterility maintenance or leakage maintenance, or both—required of the protective sealing barrier.

For instance, where it is desirable that the protective sealing barrier in accordance with the present invention act as a sterility barrier, the material selected for the membrane should be suitable for protecting against the intrusion of bacteriological contaminants, particulates, or other contaminants which might affect the sterility of syringe 30, fluid structure 50, or any medicament 44 held within the barrel. For instance, various composite or plastic films, metallic foils, treated or coated papers, or TYVEK materials can be employed. Where it is desirable to configure the protective sealing barrier as a barrier against leakage, it is preferable that the material selected for the membrane possess hydrophobic properties, in order that fluid may not pass from luer tip 54. As before, various composite or plastic films, metallic foils, treated or coated papers, or TYVEK materials can be employed for this purpose. Where the syringe is of the prefillable type, it is not necessary that the protective sealing barrier also possess sterility maintenance characteristics in and of itself; because syringe 30 may be maintained sterile, for example, by external packaging, such as blister packaging, formed around syringe 30. Nonetheless, where the syringe is of the pre-fillable type, in order to avoid the necessity for external sterility barriers, such as blister packaging, it is preferable that the protective sealing barrier be formed of a material possessing sterility maintenance characteristics as well as leakage-maintenance characteristics, i.e., the material should be able to block against bacteriological, particulate or other contaminants, while still possessing hydrophobic properties. For instance, various composite or plastic films, metallic foils, treated or coated papers, or TYVEK materials can be employed for this purpose.

Where it is desirable to process syringe 30 by an irradiation process or a heat sterilization process, the membrane can be selected from a material which exhibits good heat resistance or which otherwise is able to withstand heat and pressure changes generated during the sterilization procedure. For instance, various composite or plastic films, metallic foils, or TYVEK materials are suitable for this purpose. If it is desired to sterilize syringe 30 by various gas sterilization techniques, such as ethylene oxide gas sterilization techniques, the skilled artisan will appreciate that the membrane can be formed from a material which exhibits hydrophobic properties while at the same time is gas porous. For instance, a TYVEK material can be employed.

It will understood that the membrane realized in the foregoing manners need not be formed from a single material. For instance, a combination of materials combined into a single formulation, or a combination of materials arranged or otherwise constructed to achieve the desired properties is also possible. For instance, the membrane can be constructed in a layer configuration from differing materials so as to achieve the desired properties.

Unlike the prior art luer tip cap 24, which engages internal portions of the fluid path structure, such as at threads 18 (53) associated with a luer collar and the exterior portions of luer tip 22 (54), the protective sealing barrier makes contact only with the terminal ends of the collar and the luer tip. Accordingly, the protective sealing barrier avoids the difficulties associated with luer lock tip caps while providing good fluid sealing properties and maintaining the sterility of the syringe.

Unlike conventional luer lock tip caps 24, which are formed from rigid materials such as thermoplastics, the protective sealing barrier is relatively flexible, allowing it to be easily conformed to the dimensions, shapes or tolerances associated with terminal ends 52, 54 of the male luer tip and female luer collar. Thus, the protective sealing barrier of the present invention eliminates to a large degree many of the problems with plastic tolerances or plastic creep which might be associated with plastic parts. Coupled with the co-planar configuration of the luer tip with the luer collar, which allows substantially complete surface contact between the membrane and the terminal ends of the collar and luer tip, the protective sealing barrier of the present invention permits good safeguarding of the sterility of the fluid path and medicament, or both.

Additionally, the protective sealing barrier provides a convenient flat surface enabling a pharmaceutical manufacturer to print pertinent information concerning medicament 44 held within the syringe. The protective sealing barrier can be stocked in a variety of standard sizes accommodating a wide range of sizes of prefillable syringes Because the protective sealing barrier is relatively flat, the space required for packaging the entire prefillable syringe is reduced, requiring less inventory space and, generally, permitting more prefillable syringes to be packaged in a container of a given size. It also reduces the quantity of waste which must be discarded after the syringe is used.

Also, the protective sealing barrier provides good tamper indication for syringe 30. For example, where a conventional luer lock tip cap 24 is used, absent external means for tamper evidence, it would be difficult for an end user to determine if syringe 30 had been tampered with, because a tamperer would simply have to re-screw the tip cap back into the syringe. The protective sealing barrier of the present invention provides good indication of tamper evidence without the need to employ external means for tamper evidence; if an end user were to detect any detachment of the peelable membrane from one (or both) of terminal ends 52, 54 of the collar or luer tip, the end user would have visual means of determining whether the sterility of the syringe had been compromised.

Other permutations of the protective sealing barrier in accordance with the present invention are also possible. For instance, rigid discs can be applied, or co-injected with, the terminal ends of the luer tip and collar, in lieu of a membrane. The rigid discs could cover only the terminal end of the luer tip, if desired, so long as external packaging or other means for providing the sterility of internal portions of the collar are provided. The disc would serve to maintain the sterility of the medicament held within the syringe and provide a fluid barrier at the same time, in the manner previously described.

It will be appreciated and understood by those skilled in the art that further and additional revisions to the invention may be devised without departing from the spirit and scope of the appended claims, the invention not being limited to the specific embodiments shown.

We claim:

1. A syringe having a protective sealing barrier, comprising:
   a barrel having a proximal end and a distal end and defining therein a compartment with a quantity of medicament contained therein;
   a luer tip in fluid communication with the compartment of the barrel, the luer tip extending from the distal end of the barrel and having a terminal end;
   a collar circumferentially formed about the luer tip, the collar having a terminal end substantially coplanar with the terminal end of the luer tip; and
   a sealing membrane removably secured in substantially complete surface contact with the terminal ends of the luer tip and the collar, said membrane acting as a fluid barrier and retaining the medicament contained in the compartment of the syringe barrel.

2. The syringe of claim 1, wherein the protective sealing barrier is configured to safeguard the sterility of the syringe.

3. The syringe of claim 1, wherein the protective sealing barrier is configured as a leak-proof barrier.

4. The syringe of claim 1, wherein the protective sealing barrier is configured as a leak-proof, sterility maintenance barrier.

5. The syringe of claim 3, further containing a quantity of medicament in said compartment.

6. The syringe of claim 4, further containing a quantity of medicament in said compartment.

7. The syringe of claim 1, wherein said luer collar includes one or more threads for engaging the hub of a piercing element.

8. The syringe of claim 1, wherein said sealing membrane comprises a planar portion and a pull tab portion, said planar portion configured for substantially complete surface contact with the terminal ends of the luer tip and the collar, the pull tab portion attached to the planar portion and dimensioned to allow a user to pull the planar portion from the terminal ends.

9. The syringe of claim 1, wherein said sealing membrane is formed of a material suitable for irradiation sterilization.

10. The syringe of claim 1, wherein said sealing membrane is formed of a material suitable for gas sterilization.

11. The syringe of claim 1, wherein said sealing membrane is formed of a material suitable for heat sterilization.

12. The syringe of claim 1, wherein said sealing membrane comprises a heat-sensitive adhesive to secure the sealing membrane to the terminal ends of the luer tip and the collar.

13. The syringe of claim 1, wherein said sealing membrane comprises a pressure-sensitive adhesive to secure the sealing membrane to the terminal ends of the luer tip and the collar.

14. The syringe of claim 1, wherein the syringe is formed of a material selected from the group comprising glass and plastics.

* * * * *